United States Patent [19]

Crutchfield et al.

[11] Patent Number: 4,959,496
[45] Date of Patent: * Sep. 25, 1990

[54] CHEMICAL PROCESS

[75] Inventors: Marvin M. Crutchfield; Liou-Liang Horng, both of Creve Coeur; Robert G. Schultz, St. Louis, all of Mo.

[73] Assignee: Monsanto Company, St. Louis, Mo.

[*] Notice: The portion of the term of this patent subsequent to Aug. 21, 2007 has been disclaimed.

[21] Appl. No.: 235,854

[22] Filed: Aug. 24, 1988

[51] Int. Cl.$^5$ ............................................. C07C 59/23
[52] U.S. Cl. .................................................... 562/583
[58] Field of Search ........................................ 562/583

[56] References Cited

U.S. PATENT DOCUMENTS

| | | | |
|---|---|---|---|
| 3,635,830 | 1/1972 | Lamberti et al. | 252/89 |
| 3,692,785 | 9/1972 | Lamberti et al. | 252/89 |
| 3,914,297 | 10/1975 | Lamberti et al. | 260/535 P |
| 4,663,071 | 5/1987 | Bush et al. | 252/174.19 |
| 4,689,167 | 8/1987 | Collins et al. | 252/95 |

OTHER PUBLICATIONS

Chemical Abstracts, vol. 60, 2295G, 1964.
Chemical Abstracts, vol. 64, 4224G, 1966.

*Primary Examiner*—Bruce Gray
*Attorney, Agent, or Firm*—Raymond C. Loyer; Arnold H. Cole; Richard H. Shear

[57] ABSTRACT

There is disclosed herein improved processes for the preparation of ether carboxylates by reacting in an alkaline reaction medium the salts of maleic acid and a carboxylic or polycarboxylic acid having a reactive hydroxyl group on a non-carbonyl carbon atom in the presence of a calcium ion catalyst wherein unreacted acid salts are recovered from the reaction medium by lowering the pH of the reaction medium to a range of from about 4 to about 6. The precipitated salts are recycled to the synthesis reaction to prepare additional amounts of product.

49 Claims, No Drawings

CHEMICAL PROCESS

This invention relates to a process for making ether carboxylic acids and more particularly to processes for making ether carboxylates prepared by a calcium ion catalyzed reaction in alkaline medium of maleic acid salt and a carboxylate salt containing a reactive hydroxyl group. Such reactions are of the type typically referred to as Michael condensation reactions.

Polycarboxylic acids have long been known to be useful, usually in the salt form, as detergent builders or sequestrants. Also, ether carboxylates useful as metal sequestering and detergent builders have been known and are most desirable for their beneficial effects in laundering applications.

Because ether carboxylates have such effective sequestering ability they have become attractive in recent times for the replacement of sodium tripolyphosphate which has long been the leading detergent builder or sequesterant. Examples of prior art efforts to provide ether carboxylate detergent builders or sequesterants are found in U.S. Pat. Nos. 3,635,830; 3,692,685 which relate to the use of oxydisuccinic acid salts particularly 2,2'-oxydisuccinate salts (ODS) as detergent builders. Another example of an ether polycarboxylate detergent builder or sequesterant is found in U.S. Pat. No. 3,914,927 which relates to carboxymethyl oxysuccinates.

While many carboxylate compounds in the prior art have utility as a builder or sequesterant in laundry detergent formulations, it has been found that certain ether carboxylates are more attractive and cost effective for such utility. In the field of detergent builders and sequesterants for laundry detergent formulations low cost of the components is extremely important because it is in a very competitive market. While many ether carboxylate compounds have been found to be useful there is needed more economical manufacturing processes whereby such compounds can be economically produced in large volume.

One example of ether carboxylates is a mixture of polycarboxylic acids or salts thereof, particularly the sodium salts, of 1-hydroxy-3-oxa-1,2,4,5-pentane tetracarboxylic acid (HOPTC) and 3,6-dioxa-1,2,4,5,7,8-octane hexacarboxylic acid (DOOHC) which is highly useful in detergent formulations as a sequesterant or builder. This mixture is prepared by reaction of a combination of D,L-tartrate salts with maleate salts catalyzed by calcium ions. Due to equilibria present in the reaction and to the need for the presence of particular reactant ratios to obtain particularly preferred ratios of HOPTC and DOOHC in the product, there is considerable unreacted D,L-tartrate and maleate present at the end of the condensation reaction. Further, to provide a more economical process it is desired that a means be found to economically recover and reuse the unreacted D,L-tartrate and maleate rather than merely discharging maleate and tartrate as waste.

The synthesis of many ether carboxylates, including the mixture of HOPTC and DOOHC as well as the oxydisuccinates is achieved in an equilibrium reaction wherein starting materials, tartrate or malate and maleate salts, remain in solution at the end of the reaction. In many cases these starting materials are removed only by solvent extraction which is expensive and not ecologically attractive. Large scale production of such ether carboxylates incur large costs for recovery of reactants and an ecologically and environmentally acceptable means for recovering unreacted starting material is practically a requirement for industrial production of commercial quantities of these ether carboxylates.

SUMMARY OF THE INVENTION

In accordance with this invention, there is provided a process for preparing ether carboxylates by the reaction of the salts of maleic acid and a carboxylic or polycarboxylic acid containing a reactive hydroxyl group on a non-carbonyl carbon atom, said reaction catalyzed by calcium ions and conducted under alkaline conditions wherein unreacted salts are conveniently recovered in such manner that they may be recycled to the synthesis reaction to produce additional ether carboxylate. It has been discovered that at a limited range of acidity certain unreacted salts are conveniently recovered from the reaction mixture at the conclusion of the reaction. By reducing the pH of the reaction mixture to a range within about 4.5 to about 5.5 by combining a suitable acid with the reaction mixture, the insoluble salts of starting acid precipitate while the desired ether carboxylate product remains in solution. The precipitate is removed by known means such as filtration thereby allowing further processing of the ether carboxylate solution. Such further processing will depend, of course, upon the particular ether carboxylate produced.

In another aspect of this invention, the calcium ions employed to catalyze the condensation reaction to prepare the ether carboxylate is conveniently recovered and recycled to the synthesis reaction by precipitating the calcium as a calcium carbonate. The precipitation is accomplished by combining the reaction mixture, typically after removal of unreacted starting salts, with an alkaline earth or alkali metal carbonate at a pH in the range of from about 7 to about 12. The precipitate is removed by known means, preferably by filtration.

DETAILED DESCRIPTION OF THE INVENTION

Calcium catalyzed reactions for the production of ether carboxylates are known. A typical example of such a process is disclosed in U.S. Pat. No. 4,663,071 to Bush et al and such patent is hereby incorporated by reference. Another example of a process for preparing ether carboxylates in the presence of calcium ions is EPO 0 236 007A also to Bush et al which publication is also incorporated herein by reference.

The U.S. Patent discloses a process for preparing a mixture of HOPTC and DOOHC referred to above. In such process the mixture is obtained by the reaction of maleic acid and tartaric acid salts. The European publication discloses the preparation of oxydisuccinate through a calcium catalyzed reaction of maleic acid and malic acid salts in alkaline medium. These disclosures are typical examples of the reaction of maleic acid with a carboxylic acid or polycarboxylic acid containing a reactive hydroxyl group on a non-carbonyl carbon atom, said reaction being catalyzed by calcium ions and conducted in alkaline medium. Such reactions are known in the art as Michael condensation reactions.

It is typical of the Michael condensation reactions to provide the most effective equilibrium state for the production of the desired compound or mixture by control of the reactant ratio. For example, high ratios of maleic acid salts to malate acid salt in the range of 2 to 1 or greater respectively provide the more optimum production of ODS in the calcium ion catalyzed reaction disclosed in the European publication referred to above. However, a significant amount of unreacted maleate salt remains in solution at the end of the reaction together with the desired ODS.

As in the production of ODS, the reaction of the salts of D,L-tartaric acid and maleic acid is an equilibrium reaction wherein the amounts of the respective reactants provide control of the ratio of HOPTC and DOOHC in the reaction product.

It has been found that D,L-tartaric acid salts possess different solubility characteristics than do either the D- or L- isomers such that the D,L- isomer conveniently precipitate from solution at a pH in the range of from about 7 to about 9.5 while the calcium salts of HOPTC and DOOH remain in solution and can be purified for use as a builder combination in detergent formulations.

The recovery of unreacted maleate salts from calcium catalyzed reactions of maleic acid salts with salt of carboxylic or polycarboxylic acid containing a reactive hydroxyl group on a non-carbonyl carbon atom in alkaline medium is conveniently achieved by acidifying the reaction product so as to reduce the pH to within the range of about 4 to about 6.

A particular advantage of the process of this invention, whereby unreacted maleate salt is recovered, is the ability to regulate the reactant ratios more freely since convenient recovery and recycle is possible. Loss of unreacted maleate salt is insignificant and its recovery economical, particularly when maleic acid is employed to reduce the pH of the reaction product of the condensation reaction. High maleate to malate ratios such as in excess of 2 to 1 respectively have been found to result in the reduction or even elimination of the maturation step usually required in the production of ODS. Therefore, a preferred embodiment of this invention is the calcium catalyzed reaction of maleate and malate salts in alkaline medium wherein the ratio of maleate to malate salt is in excess of 2.

The process of this invention is disclosed in more detail below with respect to exemplary condensation reactions of maleic acid salts and carboxylic or polycarboxylic acid salts containing a reactive hydroxyl group on a non-carbonyl carbon atom. Such reactions provide, for example, mixtures of HOPTC and DOOHC and ODS.

Other typical hydroxy acids include glycolic, mucic, gluconic, isocitric, ascorbic, mandelic, citric, tartronic and sugar acids such as glucaric and saccharic acids. These acids have in common a reactive hydroxyl group on a non-carbonyl carbon atom.

In accordance with one embodiment of this invention the unreacted D,L-tartrate and maleate starting materials are removed by precipitation from the reaction mass prior to the removal of calcium from the system. Specifically, calcium D,L-tartrate and mono sodium maleate are precipitated from the reaction mixture by adjustment of the pH of the reaction solution. The precipitate of calcium D,L-tartrate and mono sodium maleate is then returned to a subsequent condensation synthesis reaction. It has been found that the small amounts of by-products such as malate and fumarate and residual amounts of HOPTC and DOOHC trapped in the precipitate are not deleterious to the use of this recycled precipitate in subsequent condensation synthesis reaction.

FORMATION OF HOPTC/DOOHC MIXTURES

The first step is the synthesis of HOPTC/DOOHC mixtures by the reaction in aqueous medium of maleate and D,L-tartrate reactants comprising both monovalent cation and calcium salts of maleic acid and D,L-tartaric acid. As noted above, the total amount of maleate plus D,L-tartrate reactants in the aqueous reaction mixture will generally range from about 20% to about 70% by weight of the mixture, more preferably from about 55% to about 65% by weight. Calcium maleate is provided by first reacting maleic acid with calcium hydroxide or calcium carbonate the later preferably provided at least in part by recycle from earlier reactions. The D,L-tartrate is provided by hydroxylation of maleic acid (from maleic anhydride) in the presence of a catalyst and hydrogen peroxide by known means. One portion of the D,L-tartaric acid employed in the synthesis reaction is taken from the neutralized hydroxylation reaction product. Another portion of the needed D,L-tartrate is provided by the recycled calcium D,L-tartrate provided by earlier reactions as will be more fully described below.

The molar ratio of maleic acid to D,L-tartaric acid in the reaction mixture provided from all the sources noted above will generally range from about 0.5:1 to 8:1, more preferably from about 0.8:1 to about 1.2:1. The ratio of reactants will control the ratio of HOPTC/DOOHC in the final product.

As noted above the synthesis reaction takes place in the presence of a catalyst comprising calcium ions. To provide the necessary amount of calcium cation, several sources are used. Calcium maleate, prepared from recycled calcium carbonate and maleic acid, provides one calcium ion source. Previously used but unreacted calcium D,L-tartrate recovered in the process of this invention provides another major calcium ion source. Any additional needed calcium ions, usually a very small amount, can be provided by an additional calcium ion source such as calcium hydroxide added either as a solid or as a slurry. Other water soluble calcium salts can be employed, but calcium hydroxide possesses the additional advantage of supplying needed hydroxide ions. The total amount of calcium ion present provides a total molar ratio of calcium cation to maleate of 1:1. However, the amount of calcium cation can vary greatly and may be such that the ratio of moles of calcium cations to total moles of maleic and D,L-tartaric acids in solution can approach, but be less than 1.

The hydroxide of a monovalent cation is also essentially added to the reaction mixture as a source of alkalinity. This neutralizing agent is usually added in an amount such that the ratio of moles of monovalent cations to total moles of D,L-tartaric acid plus the moles of maleic acid minus the moles of calcium cations ranges from about 2.1:1 to about 3.8:1. More preferably this ratio ranges from about 2.2:1 to about 3.3:1. The monovalent cation-containing neutralizing agent can be any hydroxide which upon addition to water yields monovalent neutralizing cations in solution. Such neutralizing agents include, for example, alkali metal, ammonium or substituted ammonium hydroxide. Sodium hydroxide is highly preferred.

Sufficient neutralizing agent which, in combination with calcium hydroxide, is added to the synthesis reaction mixture to insure that the reaction mixture is over-neutralized. Thus, the reaction mixture in the process of this invention will generally have a pH within the range of from about 8.5 to 13, more preferably from about 10.5 to about 12.5. The aqueous reaction mixture, after the appropriate amounts of reactants, catalysts and neutralizing agent are combined, is maintained at a temperature of from about 20° C. to about 120° C., preferably from about 70° C. to about 95° C. for a period of time sufficient to form a reaction product mixture containing the desired amounts of HOPTC and DOOHC. Reaction times of from about 0.5 to 50 hours, more preferably from about 1 to 4 hours, would generally be suitable for realizing acceptable yields of the 2 components of the desired mixture. Reaction time is highly affected by temperature whereby higher temperature increases the rate of reaction.

At completion of the reaction the mixture is quenched with water to cool it to a temperature in the range of 80° C. Addition of water also improves the handling of the viscous reaction mass.

FORMATION OF ODS

As noted above there has been previously disclosed an ether-bond forming reaction using the combination of sodium and calcium salts in aqueous alkaline ether-bond forming reactions to provide in high yield ether carboxylates. One such disclosure is EPO 0 236 007. The ether carboxylate is formed in a reaction mixture containing sodium and calcium salts of maleic acid and malic acid which react to form the sodium and calcium salts of ODS. The reaction takes place at temperatures below about 120° C. in aqueous medium wherein one component is the maleate salt and the other is the malate salt. The reaction mixture also contains an inorganic reactant component consisting essentially of at least one inorganic base or mixture thereof. The reaction mixture is held at a temperature of at least about 60° C. for a period sufficient to permit a major portion of the ether-bond formation between the maleate and malate present in the reaction mixture. According to previously known reactions the malate to maleate molar ratios range from about 1:1 to about 2:1, more preferably from about 1.1:1 to about 1.6:1 at the initial time of combination.

The molar ratio of calcium to maleate plus malate is disclosed in the prior art to be in the range of from about 0.1:1 to about 0.75:1, more preferably from about 0.31:1 to about 0.57:1. Also present in the reaction mixture is sodium which is present at a molar ratio of sodium to maleate plus malate of from about 0.5:1 to about 2.2:1. Ratios of sodium to malate and maleate are adjusted in the event the acid form of these compounds are employed and no organic salts are used. When the acid form of maleate and malate are employed the sodium to maleate plus malate molar ratio is generally in the range of from about 0.9:1 to about 1.48:1. As noted above, the reaction mixture is alkaline generally by the addition of an inorganic base so as to provide from about 0.01 to about 0.4 moles of free hydroxide per mole of combined maleate and malate. Preferably the free hydroxide is present in the range from about 0.04:1 to about 0.2:1 per mole of combined maleate and malate, preferably from 0.04:1 to 0.1:1 respectively. The reaction is reported to have been performed at a pH in the range of from about 9 to about 13 measured by cooling the reaction mixture sample to 25° C. and diluting to about 5% dissolved solids prior to pH measurement.

In accordance with this invention the malate/maleate ratio is reversed such that it is now convenient and economical to operate the reaction to produce ODS with an excess of maleate in the reaction mixture. In general the malate to maleate molar ratios in accordance with the process of this invention can range from about 1:1.5 to 1:3 respectively or even higher. Of course, the excess maleate does not react but is recovered in accordance with this invention for reuse in a convenient manner as will be more fully described below. Calcium hydroxide level is typically in the range of, on a molar basis of malate to calcium hydroxide, from 1:1 to 1:2. Calcium levels affect the reaction rate but have little effect on the ability to recover unreacted starting material in the form of sodium hydrogen maleate. An excess of base has been discovered to increase the speed of the reaction but also it increases the speed of the reversion of the desired ODS product to fumarate. In general, the reactant ratios in the reaction mixture in accordance with this invention in terms of malic acid/maleic acid/calcium hydroxide/sodium hydroxide mole ratio is typically in the range of 1/2.2/1.6/3.4. These ratios are the usual mid-point of ranges commonly employed and found to provide optimum results in accordance with this invention and can vary widely.

The reaction temperature of the process of this invention appears to control the rate of reaction and thus the amount of time required to produce optimum results. Typically, at 80° C. the reaction proceeds to completion in about 3 hours for maximum malate conversion utilizing the above-mentioned reactant ratios. When the reaction is run at about 70° C. maximum malate conversion occurs after 6 hours and such conversion is slightly higher than is found at a reaction temperature of 80° C. Acceptable results have been obtained at higher temperatures (90°/100° C.) with reaction times of 1 hour or less; however, the amount of fumarate formed increases rapidly.

The aqueous reaction mixtures forming ether carboxylates by the reaction of maleate and malate according to prior art methods contain from about 31% to about 41% by weight, more preferably 36% to about 40% by weight maleate and malate. The progress of the reaction is typically determined by applying techniques such as High Performance Liquid Chromatography (HPLC) whereby the yield of ODS and the levels of maleate and malate reactants and of fumarate by-products and other individual reaction product can be monitored. The reaction is terminated by cooling typically to below 50° C. and preferably to ambient temperature. In prior art reactions, yields of at least 50% of the ODS based upon malate were obtained. However, in accordance with the process of the present invention the yields can be higher and product processing shorter due to adjustment of reactant ratios and to the convenient recovery of unreacted starting materials. Because starting materials are conveniently recovered, greater freedom of reactant ratios in the initial reaction mixture are obtained to the benefit of greater conversion and shorter processing time to provide a final product. It is reported that the complex sodium/calcium salts of the maleate and malate reactants as well as the ODS product formed in situ provide much higher solubilities of the reaction product than when single-metal calcium salts are employed. Such solubility is advantageous because it allows convenient high-concentration processes, easier pumping and handling properties.

In accordance with this invention monosodium maleate is easily recovered from the reaction product by reducing the pH of the reaction product to a range of from about 4 to about 6 whereby the unreacted starting material precipitates as monosodium maleate and is easily recovered for recycle to the synthesis reaction. Such process will be more fully described below.

MONOSODIUM MALEATE PRECIPITATION

The reaction mixture containing mixed salts of ether carboxylates also contains relatively large amounts of unreacted maleic acid salt. Maleic acid, in the monosodium salt form, is recovered and recycled to provide higher efficiency of utilization of this valuable raw material.

The recovery of maleate salt is achieved by lowering the pH of the reaction mixture whereby sodium hydrogen maleate or monosodium maleate precipitates. In the preferred embodiment the reaction mixture is also cooled and diluted with water. An acidic material such as sulfuric acid, or an organic acid such as formic acid is added in sufficient amount to bring the combined synthesis mass and acid to a final pH in the range of from about 4.5 to 5.5, preferably slightly below 5. Any number of acidic materials can be employed to lower the pH of the reaction mixture. Combinations of acidic materials may also be employed. Typical examples of such acids are sulfuric acid, hydrochloric acid, nitric acid, formic, acetic, propionic, butyric and D,L-tartaric, carbonic, phosphoric, sulfonic, sulfurous, boric, phosphorous, adipic, benzoic, citric, fumaric, glycolic, malic, maleic, malonic, oxalic, succinic, sorbic, nitrilotriacetic, long chain fatty acids, etc.

In the process of this invention, the acid substance may be added to the crude reaction mass. Alternately, the reaction mass may be added to a heel containing the acid substance. In a further process of this invention, the acid substance and the reaction mass may be added concurrently into a mixing vessel. Sufficient water is added to the reaction mass and/or acid material so that the final concentration of desired ether carboxylate in the completed mixture is about 40%.

Sufficient acids are added to reach a preferred pH of near 5.0 and the precipitated reaction mass is cooled to below 50° C., preferably from just above the freezing point of the mixture to about 40° C. most practically to from about 20° C. to about 30° C. to obtain usable filtration rates in large scale production. In a preferred mode, cooling the reaction product from the 80° C. reaction temperature to 65° C. over 30 minutes is followed by slow cooling to from about 30° C. to about 40° C. The suspension is then allowed to rest for about 30 minutes. The slurry is preferably cooled slowly with mild or slow agitation so as to grow particles which can be filtered in an appropriately short time. Other methods of acid addition such as are noted above can also be employed with appropriate adjustment of precipitation conditions.

In the process of this invention wherein HOPTC and DOOHC are produced it has been found that both unreacted starting acids, D,L-tartaric acid and maleic acid can be recovered in their salt form. Also, it has been found that the calcium salt of D,L-tartaric acid precipitates from the reaction mixture at a pH in the range of from about 7 to about 12 and therefore can be separated while the maleate salt remains in solution. However, if desired the two acid salts may be precipitated together and recycled for use in the process of preparing additional product. Alternatively, the separation of the two acid salts may be performed in separate steps.

When a mixed acid solution is employed to precipitate tartrate and maleate in the process of this invention, the acids may be added either sequentially or concurrently. In one mode of operation, the reaction mass at a temperature of about 80° C., is added to a heel of aqueous acid, typically formic acid, and then a solution of maleic acid is added to the partly neutralized reaction mass.

It has been found that when the pH of the reaction mixture is in the above-stated range calcium D,L-tartrate precipitates when such mixture is diluted with water or cooled to a temperature in the range of from about at least above freezing to about 70° C. The reaction mixture is typically diluted with water in amounts up to about 200 percent by weight. Greater dilution may be accomplished but additional amounts of water are not beneficial due to increased solubility or the salts being precipitated and also would probably require removal later. Dilution of the reaction mixture by about 30 to about 80 percent, by weight, is typical and usually both cooling and dilution are employed to provide maximum amount of tartrate precipitation.

Alternately, if it is desired to recover only the calcium D,L-tartrate, the pH may be adjusted with acid from that of the synthesis reaction, about 12.5, down to about 9.0. At pH 9.0 almost all (above 90 percent) of the calcium D,L-tartrate is removed from the reaction mixture while almost none of the maleate is removed. Adjustment of the pH to about 9.0 instead of about 5.0 can result in considerable savings of acid, and later also base when the pH is readjusted up to about 10.0 for removal of calcium. However, unreacted maleate is not recovered. When the pH is adjusted to 9.0, precipitation procedures used are similar to those described above.

Removal of the precipitated acid salt may take any form practical and typically is performed by continuously drawing the slurry from the precipitator to a belt or drum filter or centrifuge. Other forms of removal such as decantation, etc. may also be employed. The filtrate contains the ether carboxylate in salt form. In a preferred embodiment the filtrate is transferred to another precipitator for removal of the calcium cations in the form of calcium carbonate.

In the production the HOPTC/DOOHC mixture unwashed filter cake containing the calcium D,L-tartrate and/or monosodium maleate and about 60% by weight filtrate is discharged and, in one embodiment, reslurried with water. The slurry is recycled directly or indirectly to the synthesis reactor to supply a portion of the required D,L-tartrate and maleate salts. Preferably the recovered maleate salt and/or D,L-tartrate salt is slurried with water and mixed with calcium maleate for recycle into the synthesis reaction.

In a particularly preferred embodiment of this invention, there is employed, in conjunction with the above-noted stepwise reduction of pH, the use of crystal seeding whereby small particles of calcium tartrate/monosodium maleate recovered from previous production of mixtures of HOPTC and DOOHC are added to the reaction mixture. Thus, when the temperature of the reaction mixture is first reduced to about 80° C. by diluting the reaction mixture as noted above, crystals of calcium tartrate/sodium maleate from a previous batch are introduced into the reaction mixture. Amounts of crystals in the range of up to about 10 percent of the expected weight of the fresh precipitate may be added.

Following the addition of crystals, the pH of the reaction mixture is then slowly reduced by combining the reaction mixture with acid to provide a reaction mixture having a pH in the range of about 6.5 to about 6.8. While lowering the pH of the reaction mixture it is also cooled to a temperature in the range of about 35° C. It has been surprisingly found that further reduction of the pH of the reaction mixture at a relatively rapid rate, for example in about 5 minutes, to the desired final pH in the range of about 5 provides unexpectedly large agglomerates of the combined salts of calcium tartrate and monosodium maleate. Throughout pH reduction, cooling is required to maintain the temperature of the reaction mixture in the desired range of about 35° C. As noted above, the reaction mixture is held for about 30 to about 40 minutes after final pH reduction to allow crystal formation. The larger agglomerates are more easily separated from the reaction mixture.

In the production of ODS the filter cake containing monosodium maleate is discharged and in one embodiment reslurried with water. The slurry is recycled directly or indirectly to the synthesis reaction. In a preferred embodiment the maleate salt is mixed with calcium obtained from the calcium carbonate recovered as described below.

CALCIUM CARBONATE PRECIPITATION

After removal of the insoluble acid salt or salts as described above, the filtrate from such operation is recovered and purified for use as detergent builder. In a preferred embodiment, calcium is removed either batchwise or preferably continuously. Typically, the filtrate from the above-mentioned step is pH adjusted with a base, preferably sodium hydroxide, as it is being fed into a calcium carbonate precipitator to bring the pH of the solution into a range of from about 10 to about 12, preferably from about 10 to about 10.5. The pH adjustment may be performed either in the precipitator or in a separate vessel if desired. The pH adjusted material is maintained in the range of from about 75° C. to about 110° C., preferably at about 90° C. to 100° C. Concurrently a solution of a basic carbonate, preferably sodium carbonate, preferably at a concentration of about 25%, is added to the precipitator to provide an overall mole ratio of carbonate to calcium of 1.3:1.

Alternatively, calcium carbonate is removed by increasing the mole ratio of carbonate ion to calcium ion without change in pH.

Although this invention is described with respect to carbonate precipitation using the preferred sodium cation, it is to be understood that other suitable cations may also be employed to obtain precipitation of calcium carbonate. Other cations useful in the process of this invention include potassium, ammonium or organo substituted ammonium. Other salts may be employed to obtain the calcium carbonate precipitate and includes sodium bicarbonate and mixtures of carbonates and bicarbonates.

During the precipitation of calcium carbonate it is preferred that water is continuously removed from the slurry to maintain the concentration of the organic acid salts in the range of from about 30% to about 50% by weight. Filtration of the precipitated calcium carbonate may take any form practical and typically is performed by continuously drawing the slurry from the precipitator to a centrifuge or to a belt or drum filter. The filtrate contains the desired ether carboxylate mostly as the alkaline salt along with minor amounts of raw material and by-products. In the preparation of HOPTC/DOOHC mixtures, the by-products comprise typically less than 20% by weight of the HOPTC and DOOHC present.

The wet cake from the separation is mechanically reslurried with water to form an approximately 50% calcium carbonate slurry for recycle to the synthesis reaction. The recovered carbonate may be added directly to the ether carboxylate synthesis reactor or together with recovered, unreacted tartrate and maleate. Preferably, the recovered calcium carbonate is converted to calcium maleate in a separate vessel before return to the synthesis reaction.

CALCIUM MALEATE FORMATION

Before introduction into the synthesis reaction, the calcium carbonate precipitate obtained from the product as described above is preferably converted to calcium maleate by reaction with maleic acid. Preferably, the maleic acid is prepared in situ. In one embodiment, the maleic acid is prepared by charging molten maleic anhydride to water heated to 65° C. to 75° C. After hydrolysis of the maleic anhydride to maleic acid is complete, the slurry of calcium carbonate solids is added at a rate slow enough to avoid uncontrolled foaming due to the evolution of carbon dioxide. During the addition of calcium carbonate the reaction mass is heated to a temperature in the range of from about 90° C. to about 100° C. and preferably to about 95° C.

In the production of HOPTC and DOOHC it is preferred that calcium D,L-tartrate and monosodium maleate slurry obtained from the tartrate/maleate removal step is added to the calcium maleate while heating to a boil at atmospheric pressure. The mixture is held at boiling for about 15 minutes to ensure conversion of all of the calcium carbonate to the maleate. The mixture is then charged to the synthesis reactor for the preparation of additional HOPTC and DOOHC. During transfer to the synthesis reactor water may be evaporated to reduce volume.

Although the above described process follows a particular scheme, it is obvious that other schemes or flow charts may also be followed. For example, hold tanks, mixing tanks and transfer tanks may be employed which are not described above. Other variations will occur to those knowledgeable in the art.

EXTRACTION

The filtrate obtained from the procedure to remove calcium carbonate is purified by extraction with methanol and water. Such purification in the production of ether carboxylate mixtures is shown in U.S. Pat. No. 4,633,071 referred to above.

According to such patent the solution obtained after removal of calcium carbonate is thoroughly mixed with methanol. After settling, two layers form because the desired solution of HOPTC and DOOHC is less soluble in methanol than the impurities to be removed. The undesired solution is decanted and stripped of residual methanol. The residue is dissolved in water and extracted again with methanol.

After purification the product is concentrated so as to provide the desirable concentration of ether carboxylate solution for use as detergent builder or sequestrant. The concentrated material may also be dried by any typical means such as by spray drying, etc. to provide granular or particulate material which is the form traditionally employed.

To further illustrate the process of the present invention there is described below nonlimiting preferred embodiments. In the following examples the solution obtained from the removal of calcium carbonate may be further purified such as by methanol extraction to provide a material useful as a detergent builder.

EXAMPLE 1

A 500 ml round bottomed flask was equipped with a mechanical stirrer, addition funnel, condenser, thermometer and an opening for a pH probe. To this reactor was added 45 g water, 52.5 g (0.35 mole) L-tartaric acid and 41.2 g (0.42 mole) of maleic anhydride. The mixture was heated to 50° C. to effect solution. In a separate vessel 50% sodium hydroxide (77.2 g, 0.98 mole) and calcium hydroxide (31.1 g, 0.42 mole) were mixed and stirred for fifteen minutes to prepare a smooth slurry. This slurry was then added to the reactor over a period of about thirty minutes. The temperature of the reaction mixture rose to 95° C. over the course of the addition. A further 10 ml of water was added through the addition funnel. The mixture was stirred at 90° C. for three hours and was sampled for analysis every thirty minutes. The results of NMR analyses on these samples are tabulated in Table I below. In this example it was assumed that the weight ratio of HOPTC/DOOHC was 4:1.

TABLE I

| REACTION TIME (hrs) | WEIGHT %: | | | |
|---|---|---|---|---|
| | MALE-ATE | TAR-TRATE | FUMA-RATE | HOPTC + DOOHC |
| 0.5 | 46 | 46 | — | 8 |
| 1.0 | 35 | 35 | 1 | 29 |
| 1.5 | 22 | 23 | 2 | 54 |
| 2.0 | 14 | 15 | 2 | 69 |
| 2.5 | 11 | 12 | 3 | 74 |
| 3.0 | 10 | 12 | 4 | 75 |

At the end of the reaction, 200 ml of water were added. After the temperature of the reaction mixture had fallen to 60° C., the pH of the solution was lowered to 10.5 by addition of Dry Ice. A total of 423.65 g of solution was obtained. No precipitation was observed.

EXAMPLE 2

The procedure of Example 1 was repeated with the exception that 52.5 g (0.35 mole) of D,L-tartaric acid was used in place of the same amount of L-tartaric acid. The reaction was repeated in the same manner but was run for 5.75 hours and the addition of the slurry of sodium hydroxide and calcium hydroxide was made to the reaction mass that had already been heated to about ~85° C. Samples were taken and analyzed by NMR. As in Example 1 it was assumed that the weight ratio of HOPTC/DOOHC was 4:1. The results were reported in Table II below.

TABLE II

| REACTION TIME (hrs) | WEIGHT %: | | | | |
|---|---|---|---|---|---|
| | MALE-ATE | TAR-TRATE | FUMA-RATE | HOPTC | DOOHC |
| 0.5 | 30 | 30 | 0.2 | 32 | 8 |
| 1.0 | 22 | 22 | 0.9 | 45 | 11 |
| 1.5 | 15 | 15 | 1.8 | 55 | 14 |
| 2.0 | 12 | 13 | 2.6 | 57 | 15 |
| 2.5 | 11 | 12 | 3.2 | 59 | 15 |
| 3.0 | 8 | 11 | 4.6 | 62 | 15 |
| 3.5 | 8 | 12 | 5.5 | 60 | 15 |
| 4.0 | 7 | 11 | 5.4 | 62 | 15 |
| 5.75 | 4 | 10 | 7.2 | 63 | 16 |

The analytical results indicate that considerable reaction had occurred over the first thirty minutes when the mixture was preheated to near the final reaction temperature. At the end of the reaction, 200 ml of water were added and the mixture allowed to cool to 25° C. 429.03 g of final product mixture was recovered that included both crystals (37.70 g) and solution. The crystals were removed by filtration and the resulting wet cake was analyzed. The analysis is reported in Table III below.

TABLE III

| COMPONENT | Analysis: WEIGHT % |
|---|---|
| Disodium tartrate | 74.61 |
| Disodium malate | 0.98 |
| Disodium maleate | 0.36 |
| Disodium fumarate | 2.26 |
| Tetrasodium HOPTC | 18.40 |
| Hexasodium DOOHC | 3.39 |

These results indicate that the wet cake major component was D,L-tartrate salt and that, surprisingly, this salt of D,L-tartaric acid is highly insoluble in the reaction mass while the salt of L-tartaric acid is freely soluble (Example 1 above).

It should be noted that both Example 1 and Example 2 employ an excess of maleate over tartrate as a means of conserving the expensive tartrate raw material. This ratio (excess maleate), however, leads to higher than desired formation of DOOHC.

EXAMPLE 3

This example demonstrates a higher mole ratio of tartrate to maleate to achieve the increased formation of HOPTC and uses the recovery of calcium tartrate as a route to conservation of raw materials.

Sodium hydroxide, 50%, (89.75 g, 1.12 mole), water (40g), calcium hydroxide (35.6 g, 0.48 mole) and D,L-tartaric acid (72.2 g, 0.48 mole) were charged to a 500 ml round bottomed flask equipped with a mechanical stirrer, thermometer, addition funnel and condenser. The mixture was agitated at 120 rpm and heated to 90° C. Maleic anhydride (39.4 g, 0.40 mole) was then added over fifteen minutes. Water (36.7 g) was then added and the temperature maintained at 95±1° C. for two hours. Water (250 g) and hydrochloric acid (23.8 g) were added and the temperature allowed to decrease to 50° C. The reaction mass was then cooled to 22° C. in an ice bath. The resulting solids were filtered and washed with 63 g water. Upon further standing at 22° C., a second crop of solids was obtained and recovered by filtration. The second wet cake was not washed with water. The pH of the final filtrate was measured as 10.9. The two wet cakes and the final filtrate were analyzed and the data presented in Table IV below. The results are reported as weight percent normalized for organics.

TABLE IV

| COMPONENTS | WEIGHT % FIRST WET CAKE | NORMALIZED FOR SECOND WET CAKE | ORGANICS FINAL FILTRATE |
|---|---|---|---|
| Tartrate | 86.06 | 38.02 | 4.07 |
| Malate | — | 0.87 | 1.14 |
| Maleate | 0.46 | 4.54 | 8.64 |
| Fumarate | 0.04 | 1.40 | 5.47 |
| HOPTC | 13.44 | 50.07 | 70.20 |
| DOOHC | — | 5.10 | 10.48 |

These results indicate that the addition of hydrochloric acid to reduce the pH of the reaction mass prior to filtration affords an improved recovery of tartrate of higher purity with less retention of the desired products, HOPTC and DOOHC in the wet cake.

EXAMPLE 4

50% sodium hydroxide (89.7 g, 1.12 mole), water (40 g), calcium hydroxide (35.5 g, 0.48 mole) and D,L-tartaric acid (72.1 g, 0.48 mole) were charged to a 500 ml round bottomed flask equipped with a mechanical stirrer, thermometer, addition funnel and condenser. The mixture was agitated at 120 rpm and heated to 95° C. Maleic anhydride (39.8 g, 0.40 mole) was then added over fifteen minutes. Water (36.8 g) was charged and the temperature maintained at 95±1° C. for two hours. At the end of this time water (253 g) was added and the reaction mass cooled to 22° C. in an ice bath. The product was then divided into five portions and the pH adjusted with different amounts of acetic acid as specified in the table below. Each sample was allowed to crystallize and settle for sixty to ninety minutes. After filtration, each filter cake was washed with 12 g of water and analyzed. The analysis is reported in Table V below.

TABLE V

|  | SAMPLE NO. | | | | |
| --- | --- | --- | --- | --- | --- |
|  | A | B | C | D | E |
| Sample Wt., g | 107 | 110 | 110 | 110 | 110 |
| Wt. acetic acid, added, g | 0.00 | 0.96 | 1.92 | 2.88 | 3.84 |
| Filter cake weight, g | 11 | 22 | 21.5 | 22 | 24.5 |
| pH of filtrate | 11.76 | 11.63 | 11.44 | 11.03 | 6.71 |
| Filtrate analysis Weight % | | | | | |
| Tartrate | 2.31 | 0.99 | 0.77 | 0.63 | 0.49 |
| Malate | 0.28 | 0.27 | 0.27 | 0.26 | 0.26 |
| Fumarate | 1.28 | 1.35 | 1.33 | 1.35 | 1.32 |
| Maleate | 1.52 | 1.58 | 1.55 | 1.57 | 1.59 |
| HOPTC | 14.97 | 15.34 | 14.86 | 14.91 | 14.47 |
| DOOHC | 2.02 | 2.10 | 1.99 | 2.15 | 2.00 |
| % of tartrate present that was removed | 70.0 | 88.0 | 91.0 | 92.5 | 94.5 |
| Tartrate as % of total organics in solution (26% before pptn) | 10.4 | 4.5 | 3.8 | 3.0 | 2.4 |

This example shows that addition even of small amounts of acid greatly increases the efficiency of tartrate removal by crystallization. It should also be noted that the other components of the reaction product mixture do not change upon the acid treatments.

EXAMPLE 5

The procedure of Example 4 was repeated except that differing amounts of tartaric acid instead of acetic acid were added tot he five separated parts of the final product. The results obtained using this different acid are shown in Table VI below.

TABLE VI

|  | SAMPLE NO. | | | | |
| --- | --- | --- | --- | --- | --- |
|  | A | B | C | D | E |
| Sample Wt., g | 108 | 111 | 111 | 111 | 111 |
| Wt. tartaric acid added, g | 0.00 | 1.2 | 2.4 | 3.6 | 4.8 |
| Filter cake weight, g | 20 | 33 | 30 | 35 | 40 |
| pH of filtrate | 11.76 | 11.71 | 11.50 | 10.59 | 6.63 |
| Filtrate analysis Weight % | | | | | |
| Tartrate | 1.83 | 1.79 | 1.97 | 2.21 | 2.74 |
| Malate | 0.28 | 0.29 | 0.29 | 0.26 | 0.27 |

TABLE VI-continued

|  | SAMPLE NO. | | | | |
| --- | --- | --- | --- | --- | --- |
|  | A | B | C | D | E |
| Fumarate | 1.28 | 1.36 | 1.25 | 1.26 | 1.29 |
| Maleate | 1.60 | 1.70 | 1.53 | 1.58 | 1.62 |
| HOPTC | 15.59 | 16.19 | 14.91 | 14.87 | 15.07 |
| DOOHC | 2.02 | 2.16 | 1.98 | 2.04 | 2.12 |
| % of tartrate orig. present that was removed | 77.5 | 78.5 | 77.0 | 76.0 | 72.5 |
| Tartrate as % of total organics in solution (26% before pptn) | 7.7 | 7.7 | 9.0 | 9.8 | 11.9 |

When citric acid or formic acid was used in place of tartaric acid, similar results were obtained. Both these examples also show that adding carboxylic acids to the cooled reaction mixture increases the efficiency of tartrate removal from the solution. These examples also show that the maleate content is not reduced.

EXAMPLE 6

Calcium hydroxide (1.11 g, 0.015 mole), D,L-tartaric acid (45.4 g 0.303 mole), 50% sodium hydroxide solution (92.48 g, 1.156 mole NaOH) and water (50 g) were placed in a 500 ml 4-neck flask equipped with a stirrer (120 rpm), thermometer, condenser and addition funnel. A calcium tartrate wet cake (65.15 g) of the following analysis was then added:

| COMPONENT | WEIGHT |
| --- | --- |
| Calcium tartrate | 25.67 g |
| Disodium malate | 0.26 g |
| Disodium fumarate | 1.17 g |
| Disodium maleate | 1.63 g |
| HOPTC | 18.18 g |
| DOOHC | 3.52 g |
| Water | 14.79 g |

In a separate vessel a calcium maleate slurry was prepared in the following manner. A calcium carbonate recycle filter cake, 38.2 g, of the following analysis was slurried with 40 g water:

| COMPONENT | WEIGHT |
| --- | --- |
| Calcium carbonate | 24.8 g |
| Disodium tartrate | 0.31 g |
| Disodium fumarate | 0.38 g |
| Disodium maleate | 0.30 g |
| Disodium malate | 0.08 g |
| HOPTC | 4.81 g |
| DOOHC | 0.23 g |
| Water | 7.29 g |

Over a 40 minute period, this slurry was added to a mixture of maleic anhydride (39.2 g, 0.4 mole) and water (80 g) that had been heated to a 60° C. to convert all the anhydride to maleic acid. Calcium maleate was formed. An additional 0.5 g (0.005 mole) of calcium carbonate was added to make up the total amount of calcium needed in the synthesis reaction.

The calcium maleate slurry was then added to the reaction mixture described above and the total mass was heated to 78° C. Within one hour the mixture turned to a clear solution. The reaction was stirred for 3½ hours at 78° C. 250 g water was added and the mixture cooled to 27° C. Then acetic acid (12.9 g) was added to reduce the pH from 12.24 to 8.74.

The resulting mass was filtered, giving a calcium tartrate filter cake (for recycle) and a clear filtrate. This filtrate was added to a solution of sodium bicarbonate (2.1 g), sodium carbonate (25.97 g) and water (90 g) at 55° C. The mixture was heated at 75° C. for one hour and then at 85° C. for an additional hour to precipitate calcium carbonate. The mixture was filtered hot giving a calcium carbonate wet cake and a filtrate. The filtrate contained the desired HOPTC and DOOHC products as sodium salts and had the following analysis:

| COMPONENT | WEIGHT % |
|---|---|
| HOPTC | 22.09 |
| DOOHC | 5.38 |
| Disodium tartrate | 0.99 |
| Disodium maleate | 1.71 |
| Disodium fumarate | 1.70 |
| Disodium malate | 0.20 |

The reactions described above were repeated four more times, each time using the two filter cakes (the "tartrate cake" and the "carbonate cake") obtained from the previous reaction as recycles to the next synthesis reaction. In each case similar results were obtained. In all cases the reactions were run for three hours at 90±2° C. The results are reported in Table VII below in weight percent.

TABLE VII

| Reaction | 1 | 2 | 3 | 4 |
|---|---|---|---|---|
| Initial Solids % | 34.0 | 28.0 | 28.0 | 43.0 | 45.0 |
| Final Solids % | 72.0 | 71.0 | 67.0 | 67.0 | 68.0 |
| Total HOPTC + DOOHC % | 72.0 | 72.0 | 68.0 | 67.0 | 68.0 |
| Ration of HOPTC/DOOHC | 4.1 | 4.7 | 5.4 | 4.5 | 5.6 |
| Maleate Conv. % | 78.0 | 75.0 | 73.0 | 74.0 | 76.0 |

This example demonstrates that calcium tartrate wet cake prepared under synthesis conditions can be recycled into the synthesis reaction.

EXAMPLE 7

A procedure similar to Example 6 was carried out using both calcium tartrate and calcium carbonate wet cakes as well as an alkaline solution of disodium tartrate, 50% sodium hydroxide, calcium hydroxide and calcium carbonate. After all preliminary reactions (carbon dioxide removal, equilibrations, etc.) the charge to the synthesis reaction consisted of

| Calcium tartrate | 14.93 g |
|---|---|
| Disodium tartrate | 72.26 g |
| Calcium maleate | 43.75 g |
| Disodium maleate | 18.54 g |
| Disodium fumarate | 0.21 g |
| Sodium hydroxide | 4.71 g |
| Water | 308.63 g |

This charge is equivalent to a tartrate/maleate/calcium ratio of 1.13/1.00/0.91.

The mixture was heated to 80° C. with an air flushing stream attached to the reactor. 150 g of water was collected in a receiver to effect partial concentration of the system. The air stream was stopped and then the reactor was heated at 90±1° C. for two hours.

250 g water was added and then 9.15 g of formic acid was added over 30 minutes. During the formic acid addition, the pH in the reactor dropped from 11.65 to 8.02. After cooling to 30° C., the reaction mass was filtered giving a calcium tartrate wet cake (70.7 g) suitable for recycle to the synthesis reaction and a filtrate (423 g) containing the desired products HOPTC and DOOHC.

A solution containing 2.1 g sodium bicarbonate and 26.0 g sodium carbonate in 90 g water was prepared and heated to 70° C. The above filtrate was added to this solution over 45 minutes while maintaining the temperature at 70° C. The mixture was then heated at 90° C. for forty minutes and filtered while hot. The calcium carbonate wet cake obtained (28.1 g) was also suitable for recycle to a synthesis reaction.

The final product solution (465.7 g) was found to contain the following ingredients:

| COMPONENT | WEIGHT % |
|---|---|
| Disodium tartrate | 2.03 |
| Disodium malate | 0.42 |
| Disodium fumarate | 0.65 |
| Disodium maleate | 1.98 |
| HOPTC | 15.65 |
| DOOHC | 4.62 |

This example shows that the enhanced removal of tartrate from the final product is possible using formic acid in reaction systems employing wet cake recycle streams.

EXAMPLE 8

Sodium hydroxide at 50% concentration (89.6 g, 1.12 mole), water (40 g), calcium hydroxide (29.6 g, 0.40 mole) and D,L-tartaric acid (66.0 g, 0.44 mole) were charged to a 500 ml round bottomed flask equipped with a mechanical stirrer, thermometer, addition funnel and condenser. The mixture was agitated at 120 rpm and heated to 95° C. Maleic anhydride (39.2 g, 0.40 mole) was then added over fifteen minutes. The temperature was maintained at 90±1° C. for 140 minutes. At the end of this time water (100 g) was added and the pH measured to be 12.18. The pH was then adjusted to a value of 5.2 by addition of 17.2 g of 88% formic acid (0.329 mole) while cooling to 25° C. The reaction mass was then filtered. Below in Table VIII is shown the analysis of the raw reaction mass and the filtrate.

TABLE VIII

| COMPONENT | WEIGHT % IN REACTION MASS AT END OF REACTION | WEIGHT % IN FILTRATE AFTER FILTRATION |
|---|---|---|
| Disodium tartrate | 9.02 | 0.58 |
| Disodium malate | 0.23 | 0.52 |
| Disodium fumarate | 1.83 | 1.88 |
| Disodium maleate | 2.61 | 0.47 |
| HOPTC | 23.66 | 24.12 |
| DOOHC | 4.17 | 4.15 |

This example shows that reduction of the pH of the reaction mass to below 6.0 (for example to the preferred value of pH 5.2) reduces both the tartrate and the maleate to lower levels. Both materials are recovered in the filter cake, the tartrate as calcium tartrate and the maleate as monosodium maleate. This filter cake can then be recycled to a subsequent synthesis reaction to prepare HOPTC and DOOHC and represents a considerable conservation of raw materials. In light of the similar solubilities of monosodium maleate (6.73/100 g water)

and monosodium fumarate (6.87/100 g water), the selective removal of monosodium maleate over monosodium fumarate is surprising.

EXAMPLE 9

Sodium hydroxide, 50%, (179.2 g, 2.24 mole), water (80 g), calcium hydroxide (59.2 g, 0.80 mole) and D,L-tartaric acid (132.0 g, 0.88 mole) were charged to a 500 ml round bottomed flask equipped with a mechanical stirrer, thermometer, addition funnel and condenser. The mixture was agitated at 120 rpm and heated to 94° C. Maleic anhydride (78.4 g, 0.80 mole) was then added over fifteen minutes. The temperature was maintained at 90±2° C. for three hours. At the end of this time water (200 g) was added and the mixture cooled and divided into four portions. Each portion was pH adjusted with formic or sulfuric acid as specified in the table below. Each sample was allowed to crystallize and was filtered. The filtrate and filter cake were analyzed and the results shown in the Table IX below.

TABLE IX

| SAMPLE NO. | A | B | C | D | FINAL PROD. FROM SYNTHESIS |
|---|---|---|---|---|---|
| Sample Wt., g | 177 | 177 | 177 | 175 | (before acidification) |
| Wt. sulfuric acid added, g. | 8.4 | — | 8.4 | 6.1 | |
| Wt. formic acid, added, g | — | 8.6 | — | — | |
| Water added, g. | 10 | 10 | 60 | 10 | |
| Filter cake weight, g | 73 | 61.5 | 68 | 65 | |
| pH of filtrate | 5.04 | 5.05 | 5.0 | 6.5 | |
| Filtrate analysis | | | | | |
| Weight % | | | | | |
| Tartrate | 0.61 | 0.57 | 0.64 | 0.53 | 8.79 |
| Malate | 0.49 | 0.61 | 0.39 | 0.53 | 0.54 |
| Fumarate | 2.35 | 2.39 | 1.83 | 2.22 | 2.24 |
| Maleate | 0.57 | 0.76 | 0.91 | 2.41 | 2.64 |
| HOPTC | 24.71 | 24.48 | 19.06 | 23.91 | 24.04 |
| DOOHC | 3.93 | 3.90 | 3.03 | 3.86 | 3.65 |
| % of tartrate present that was removed | 93.1 | 93.5 | 92.7 | 94.0 | |
| Tartrate as % of total organics in solution | 1.9 | 1.7 | 2.5 | 1.6 | 21.0 |
| Maleate as % of total organics in solution | 1.7 | 2.3 | 3.5 | 7.2 | 6.3 |

The unwashed filter cakes from samples A and C above were analyzed as shown in Table X below:

TABLE X

| COMPONENT WT. % | SAMPLE A CAKE | SAMPLE C CAKE |
|---|---|---|
| Tartrate | 14.8 | 14.4 |

TABLE X-continued

| COMPONENT WT. % | SAMPLE A CAKE | SAMPLE C CAKE |
|---|---|---|
| Malate | 0.4 | 0.3 |
| Fumarate | 1.2 | 0.9 |
| Maleate | 4.0 | 3.1 |
| HOPTC | 14.3 | 10.8 |
| DOOHC | 1.9 | 1.4 |

This example shows that both sulfuric acid and formic acid are effective in pH adjustment for removal of tartrate and maleate from the reaction mixture. In addition, analysis of Sample D shows the need for reducing the pH to achieve efficient removal of maleate.

EXAMPLE 10

The unwashed filter cakes from the tartrate/maleate removal step and the calcium carbonate precipitation step of Samples A and C in Example 9 above were combined with water to give a slurry (total wt. 221 g.). This slurry containing 50% sodium hydroxide (88 g, 1.1 mole), calcium hydroxide (19.5 g, 0.26 mole) and D,L-tartaric acid (43.5 g, 0.29 mole) was charged to a 500 ml round bottomed flask equipped with a mechanical stirrer, thermometer, addition funnel and condenser. The mixture was agitated at 120 rpm and heated at 85° C. Maleic anhydride (34.9 g, 0.36 mole) was then added over fifteen minutes. The temperature was maintained at 85-90° C. for one hour while sweeping air through the reactor to remove excess water. When the solids content of the reaction reached 60-65%, the air stream was stopped and the reaction heated at 90° C. for two hours. At the end of this time water (70 g) was added and the mixture charged into a mixture of sulfuric acid (18.1 g) and water (30 g). The final pH was 5.18. The mixture was cooled to 25° C. and the precipitate removed by filtration. The filtrate was charged into a solution of sodium carbonate (26.8 g, 0.25 mole) and water (70 g) to precipitate calcium carbonate. The calcium carbonate was separated by filtration. The filtrate contained the desired HOPTC and DOOHC. Analyses of each are tabulated in Table XI below.

TABLE XI

| COMPONENT WT. % | END OF REACTION | FILTRATE FROM TARTRATE/MALEATE REMOVAL | FILTRATE AFTER CARBONATE REMOVAL |
|---|---|---|---|
| Tartrate | 11.66 | 1.18 | 0.80 |
| Malate | 1.23 | — | 0.24 |
| Fumarate | 2.77 | 2.51 | 2.35 |
| Maleate | 1.87 | 0.32 | 0.35 |
| HOPTC | 29.64 | 25.66 | 23.24 |
| DOOHC | 4.82 | 4.25 | 4.18 |

Overall maleate conversion was 74.1%.

This example shows that the wet cake obtained in the removal of both calcium tartrate and monosodium maleate can be recycled in the synthesis reaction.

EXAMPLE 11

A procedure similar to Example 6 was carried out using both calcium tartrate and calcium carbonate wet cakes as well as an alkaline solution of disodium tartrate, and 50% sodium hydroxide. After all preliminary reactions (carbon dioxide removal, equilibrations, etc.) the charge to the synthesis reactor consisted of:

| Calcium tartrate | 132.35 g |

-continued

| | |
|---|---|
| Disodium tartrate | 68.68 g |
| Calcium maleate | 92.40 g |
| Disodium maleate | 112.32 g |
| Sodium hydroxide | 34.34 g |
| Water | 636.67 g |

This charge is equivalent to a tartrate/maleate/calcium/sodium hydroxide mole ration of 1.0/1.0/1.0/0.65.

The mixture was heated to 80° C. with an air flushing stream attached to the reactor to effect partial concentration of the system and the reaction heated at 85° C. for two hours. Then 70 g water was added to quench the reaction. The reaction mixture was then added to a mixture of water, 220 g and 61 g of 88% formic acid (1.17 moles) over 30 minutes. The final pH observed at the end of the addition was 5.0. The system was then cooled to 24° C. and the reaction mass was filtered giving a wet cake containing calcium tartrate and sodium hydrogen maleate suitable for recycle to the synthesis reaction and a filtrate containing the desired products HOPTC and DOOHC. Analyses (in weight %) of the diluted reaction mass, filtrate and wet cake appear in Table XII below in weight percent:

TABLE XII

| COMPONENT | REACTION MASS AFTER QUENCH | FILTRATE | WET CAKE |
|---|---|---|---|
| Sodium formate | 2.71 | 12.84 | 5.62 |
| Disodium tartrate | 11.77 | 1.43 | 25.28 |
| Disodium malate | 0.54 | 0.36 | 0.62 |
| Disodium fumarate | 1.23 | 1.17 | 0.63 |
| Disodium maleate | 5.92 | 0.50 | 11.95 |
| HOPTC | 28.59 | 25.64 | 16.07 |
| DOOHC | 5.48 | 4.11 | 2.29 |

EXAMPLE 12

Two mixtures of reagents were prepared:

MIXTURE A

Maleic Anhydride, 67.0 g (0.67 mole)
Tartaric Acid, 60.0 g (0.40 mole)
Calcium Hydroxide, 77.2 g (1.04 mole)
Water, 300 g.

MIXTURE B

Maleic Anhydride, 33.0 g (0.33 mole)
Tartaric Acid, 105.1 g (0.70 mole)
50% Sodium Hydroxide, 164.8 g (2.06 moles)
Water, 120 g (6.66 moles)

The two mixtures were poured into a 1 liter Ace reactor fitted with an air inlet sweep, thermometer, mechanical stirrer and a distillation condenser with receiver. The mixture was heated to 85° C. and 67.2 g (0.84 mole) 50% sodium hydroxide added and the air sweep begun. The reaction was heated to 90-95° C. and 300 ml water collected off the reaction over 105 minutes. Total reaction time was 135 minutes at 90-95° C.

The reaction mixture was then poured slowly into a beaker containing 12 g water and 32 g of 88% formic acid (0.612 mole). The final pH was adjusted to 9.0 by adding an additional 6.1 g of 88% formic acid (0.117 mole) when the reaction mixture addition was complete. The mixture was cooled to 30° C. and the resulting calcium tartrate removed by filtration.

The filtrate was then added to a solution of 69.5 g (0.66 mole) of sodium carbonate in 162 g water in a 1 liter flask equipped with addition funnel, thermometer, mechanical stirrer and distillation apparatus with receiver. The mixture was heated to 100-108° C. to remove excess water and precipitate calcium carbonate. After removal of 203.6 g of water over a two hour period, the mixture was cooled to 93° C. and filtered while still hot.

A solution of citric acid, 27.2 g and water, 35.6 g was placed in a 1 liter flask and the filtrate containing the desired HOPTC and DOOHC was added. The pH was measured at 5.27. The mixture was heated to 90° C. for 30 minutes to remove carbonate as carbon dioxide and then cooled to 25° C. The crystallized monosodium maleate was removed by filtration and the filtrate analyzed as shown in Table XIII below:

| COMPONENT | WEIGHT % |
|---|---|
| Tartrate | 2.73 |
| Malate | 0.60 |
| Fumarate | 3.19 |
| Maleate | 0.65 |
| HOPTC | 40.73 |
| DOOHC | 5.50 |

The ratio of HOPTC to DOOHC was 7.4 and the maleate conversion to desired products was 75.2%. Only 0.7% calcium remained in the final product.

This example shows another process to remove both calcium tartrate and mono sodium maleate, in this case in two steps.

EXAMPLE 13

Maleic Anhydride (52 g, 0.53 mole), water (320 g) and 50% sodium hydroxide (13.14 g, 0.16 mole) were placed in a one liter, 4-neck flask equipped with a mechanical stirrer, thermometer, addition funnel and condenser with receiver. The mixture was agitated at 120 rpm and heated to 85° C. to form a mixture of maleic acid and monosodium maleate. Calcium carbonate (30.8 g, 0.308 mole) was added and heating and stirring continued to effect calcium maleate formation. Wet cake from an earlier run containing calcium tartrate (77.64 g, 0.413 mole) and monosodium maleate (28.98 g, 0.21 mole) was added. Then a solution containing disodium tartrate (73.7 g, 0.38 mole) and disodium maleate (18.0 g, 0.112 mole) and water (330 g) was added. Heating was continued at 90° C. with air sweeping over the reaction surface and water was removed and collected. 50% sodium hydroxide (52.5 g, 0.656 mole) was added and heating continued for three hours. Over this time, 400 cc water was collected in the receiver. At the end of the reaction, 45 g water was added to quench the reaction (Sample A).

An acid "heel" was prepared by adding 88% formic acid (22.6 g, 0.432 mole) and maleic anhydride (17.0 g, 0.173 mole) to water (120 g). When all the maleic anhydride had reacted to give maleic acid, the reaction product from above was added to this prepared "heel". The resulting mixture had a pH of about 5.2. After cooling, the mixture was filtered to remove the crystallized calcium tartrate and monosodium maleate. The unwashed filter cake weighed 268 g (Sample B) and the filtrate weighed 314 g (Sample C). The filtrate (300 g) was then added to a solution of sodium carbonate (37 g, 0.349 mole) in water (100 g) and the mixture heated to 70° C. to begin calcium carbonate removal. To complete the reaction an additional 1.7 g (0.02 mole) of 50% sodium hydroxide and 10 g (0.094 mole) of sodium carbonate were added. Filtration gave 56 g of calcium carbonate wet cake and 317 g of filtrate (Sample D) that contained the desired HOPTC and DOOHC. Analysis for each sample appears in Table XIV below in weight percent:

TABLE XIV

| COMPONENT | SAMPLE A | SAMPLE B | SAMPLE C | SAMPLE D |
|---|---|---|---|---|
| Formate | 4.21 | 5.88 | 14.68 | 8.06 |
| Tartrate | 14.62 | 21.39 | 1.55 | 0.99 |
| Malate | 1.38 | 0.87 | 0.62 | 0.41 |
| Fumarate | 1.97 | 0.96 | 2.28 | 1.47 |
| Maleate | 4.67 | 17.86 | 0.35 | 0.22 |
| HOPTC | 37.28 | 17.71 | 37.96 | 23.90 |
| DOOHC | 6.46 | 3.56 | 7.98 | 5.16 |

This example shows that a combination of acids, in this case formic acid and maleic acid may be used to reduce the pH to 5.2 and to aid the crystallization of calcium tartrate and monosodium maleate. The advantage of using maleic is that it is needed in the recycle system and its insertion here provides the advantage of its acid values. This reduces the amount of formic acid needed, a cost saving, and also reduces the sodium load in the system.

EXAMPLE 14

This example shows that a combination of acids, in this case formic acid and maleic acid, may be used to reduce the pH to 5.2 and to aid the crystallization of calcium tartrate and monosodium maleate. The advantage of using maleic is that it is needed in the recycle system and its insertion here allows one to take advantage of its acid values. This reduces the amount of formic acid needed, a cost saving, and also reduces the sodium load in the system.

Wet cakes containing calcium tartrate and monosodium maleate and calcium carbonate prepared in a manner similar to that described in Example 13 above except that the calcium tartrate-monosodium maleate wet cake was partially washed to reduce the amount of HOPTC+DOOHC remaining in the cake. These wet cakes were then used in the experiments described below:

| Calcium Tartrate Wet Cake | | Calcium Carbonate Wet Cake | |
|---|---|---|---|
| COMPONENT | WT. % | COMPONENT | WT. % |
| Sodium formate | 1.37 | Sodium Formate | 1.77 |
| Calcium tartrate | 21.12 | Disodium tartrate | 1.11 |
| Monosodium maleate | 19.96 | Disodium maleate | 0.71 |
| Disodium fumarate | 1.54 | Disodium fumarate | 0.75 |
| HOPTC | 8.42 | HOPTC | 9.58 |
| DOOHC | 1.16 | DOOHC | 2.27 |
| Water | 46.43 | Calcium carbonate | 58.67 |
| | | Water | 25.14 |

Part A 64.10 g water was charged to a 1-liter 4-neck flask fitted with condenser, stirrer and thermometer. After heating to 65° C., 43.61 g of maleic anhydride was added and the system held at 65° C. for five minutes. Then 340 g of calcium tartrate wet cake slurry along with 26.88 g water was added at 65° C. (pH 2.49). After holding for 10 minutes at 65° C., 100 g of calcium carbonate slurry was added and heated at boiling (~102° C.) for 30 minutes (pH 6.94). A sample taken at this point showed only 0.1% carbonate to be present.

Part B 100 g water was charged to the reactor described in Part A above. After heating to 65° C., 31.2 g maleic anhydride was added and the system held at 65° C. for five minutes. Then 100 g of the calcium carbonate slurry was added and the mixture heated to boiling (pH 8.2). After thirty minutes at reflux, 340 g of calcium tartrate wet cake slurry was added along with 20.60 g water. Boiling was continued for thirty minutes more. At this point analysis showed presence of only 0.1% carbonate (pH 6.65). (At the point of carbonate wet cake addition, 5% carbonate was present.)

These examples show that it is possible to combine tartrate wet cake with carbonate wet cake before carbon dioxide removal and that addition sequence is not important for efficient removal of the carbon dioxide.

EXAMPLE 15

Maleic anhydride (109.21 g, 1.114 mole) was added to 200 ml of water in a three liter 4-neck flask that was equipped with a mechanical stirrer, thermometer, air sweep inlet and condenser with receiver. The mixture was heated to 85° C. and then 115.57 g, (0.77 mole) of tartaric acid was added along with 25 ml more water. Calcium carbonate (135.54 g, 1.355 mole) was slurried with 112 ml water and added slowly to the reactor. Alternating portions of disodium tartrate solution and calcium hydroxide were added to the reactor while maintaining the heat at 85° C. The total charge of calcium hydroxide was 51.87 g (0.700 mole). The disodium tartrate solution added contained disodium tartrate (277.42 g, 1.43 moles) and disodium maleate (141.81 g, 0.8863 mole). After the reaction to drive off the carbon dioxide and form calcium maleate was complete, the air sweep was begun while holding the reaction temperature at about ~91° C. A total of 730 ml water was collected in the receiver. Then sodium hydroxide, 93.91 g (1.1674 mole) was added and the reaction held at about ~91° C. for eighty minutes more. An additional 270 ml water was removed from the system over the course of the synthesis reaction. The reaction was then quenched and cooled with 230 ml of water (Sample A).

A "heel" was prepared by adding 49.03 g (0.50 mole) of maleic anhydride to 460 ml water. The solution was heated to 76° C. to complete the reaction to maleic acid and the 61.30 g (0.626 mole) of sulfuric acid was added. The reaction mass from the synthesis above was added slowly to the acid "heel" with continuing agitation. Final pH was 5.2. The slurry was cooled from 80° C. down to 35° C. over five hours. The mass was then filtered to provide a filter cake (Sample B) and the filtrate (Sample C) carried forward to the calcium removal step.

The pH of the filtrate was adjusted to 10.3 (from 5.6) by adding sodium hydroxide. The filtrate was then added to a hot (88° C.) solution of sodium carbonate (51.34 g, 0.484 mole) and water. After holding for one hour at 91-92° C. the mixture was then filtered hot and the filtrate analyzed (Sample D). The analysis of each sample appears in Table XV below. Analyses (Weight %).

TABLE XV

| COMPONENT | SAMPLE A | SAMPLE B | SAMPLE C | SAMPLE D |
|---|---|---|---|---|
| Tartrate | 17.66 | 21.62 | 1.33 | 1.14 |
| Malate | 1.83 | 0.48 | 0.62 | 0.29 |

TABLE XV-continued

| COMPONENT | SAMPLE A | SAMPLE B | SAMPLE C | SAMPLE D |
|---|---|---|---|---|
| Fumarate | 0.96 | 0.69 | 1.06 | 1.04 |
| Maleate | 7.47 | 9.19 | 1.99 | 1.94 |
| HOPTC | 29.16 | 16.22 | 23.23 | 21.53 |
| DOOHC | 5.03 | 3.00 | 3.95 | 4.15 |

EXAMPLE 16

Into a 1 liter Ace reactor equipped with a thermometer, mechanical stirrer, condenser and a sample port there is placed 156.5 g of water. Then 240 g of 50% sodium hydroxide solution (3.0 moles) were added. D,L-malic acid (134.0 g, 1.0 mole) was added slowly to this mixture. At the end of the addition, the temperature had risen to ca. 85-90° C. Calcium hydroxide (118.4 g, 1.6 mole) was added as a solid to the solution and the slurry stirred vigorously. Maleic anhydride (196.0 g, 2.0 moles) was added as a solid at such a rate that the temperature was maintained between 80 and 95° C. (ca. 15 min.) On completion of this addition, the reaction mass comprised about 60% solids, 40% water. The partially cleared (translucent) mass was stirred and held at 80-85° C. for three hours. At the end of this time, 100 g of water was added and cooling begun. When the reaction mass reached 50° C., formic acid (62 g of 88%, 1.24 mole) was added to adjust the pH to 5.0 (4.5-5.0 by pH strips). During the addition of formic acid the reaction mass cleared to a pale yellow solution and then white solids crystallized out (sodium hydrogen maleate). The mass was further cooled to about 33° C.

The mixture was filtered and the pale yellow filtrate, 600.4 g, was sampled for analysis. This filtrate was then pH adjusted to 10.0 with 50% sodium hydroxide and added to a hot ( about 70° C.) solution of sodium carbonate (219.0 g, 2.067 moles, 1.3 moles carbonate/mole calcium) in 700 ml of water. Calcium carbonate rapidly precipitated. The mixture was stirred and held at 75-80° C. for 75 minutes. The mixture was filtered hot and the calcium carbonate formed washed with 125 ml water. The filtrate, 1470.1 g was samples for analysis.

Analytical results of the reaction mixture as treated above (normalized weight %) appear in Table XVI below.

TABLE XVI

| SAMPLE: COMPONENT | END OF REACTION | AFTER MALEATE REMOVAL | AFTER CARBONATE REMOVAL |
|---|---|---|---|
| Disodium Malate | 3.20 | 8.08 | 8.53 |
| Disodium Maleate | 28.66 | 1.63 | 1.38 |
| Disodium Fumarate | 4.33 | 5.90 | 6.25 |
| Tetrasodium Oxydisuccinate | 63.81 | 84.40 | 83.85 |
| Malate Conversion (Mole %) | 91.31 | 84.62 | 83.82 |

This example shows that high malate conversions are possible, driven by the presence of excess maleate and that this excess maleate can be removed by precipitation as sodium hydrogen maleate, recovered and recycled into the synthesis ODS.

Example 17 below shows the use of maleic acid as an acidification agent. Use of maleic acid instead of formic acid (or sulfuric acid or any other acid) avoids introduction of an additional component into the reaction mixture. When maleic acid is used to acidify a reaction mixture containing an initial molar ratio of malic acid to maleic acid of 1:2, two moles of sodium hydrogen maleate are produced for recycle. Malic acid of higher purity is preferred in this embodiment to prevent build up of excess maleic acid in the system.

EXAMPLE 17

The procedure of Example 1 was repeated using the same charges to give a Malic/Maleic/Ca(OH)$_2$/NaOH mole ratio of 1.0/2.0/1.6/3.0. The reaction was run at 80-85° C. for three hours. At the end of the reaction period a solution of maleic acid, prepared by dissolving 98 g (1.0 mole) of maleic anhydride in 200 g water at 65-70° C. was added to the hot reaction mixture. The pH after the addition of maleic acid was measured at 4.94. The reaction mass was cooled to about 30° C. and filtered. The crystals of sodium hydrogen maleate were washed with about 150 ml water and air dried. The filter cake weighed 432.3 g and the filtrate weighed 560.6 g. Both were sampled for analysis.

A solution of 220.5 g (2.08 moles) of sodium carbonate in 600 ml water was prepared and heated to about 80° C. The filtrate from above was slowly added to the sodium carbonate solution at 80° C. to precipitate calcium carbonate from the reaction mixture. The resulting slurry was heated at 80-85° C. for one hour and then filtered hot. The calcium carbonate filter cake was washed with about 50 ml water. The filtrate, containing the desired ODS as the tetrasodium salt was analysed. Analysis by x-ray fluorescence indicates only 0.056% calcium present in the filtrate. Analytical results of the reaction mixture (normalized weight %) appear in Table XVII below.

TABLE XVII

| SAMPLE: COMPONENT | END OF REACTION | AFTER MALEATE REMOVAL | AFTER CARBONATE REMOVAL |
|---|---|---|---|
| Disodium Malate | 6.22 | 8.34 | 8.41 |
| Disodium Maleate | 28.75 | 2.18 | 2.37 |
| Disodium Fumarate | 5.07 | 7.15 | 7.11 |
| Tetrasodium Oxydisuccinate | 59.96 | 82.33 | 82.11 |
| Malate Conversion (Mole %) | 83.54 | 83.87 | 83.72 |

This example shows that maleic acid can be used to remove sodium hydrogen maleate from the reaction and still maintain acceptably low residual levels of maleate in the final product.

Example 18 below shows the use of a higher ratio of maleic acid in the reaction mixture, 1/2.5 malate/maleate. In addition, a mixture of formic and maleic acids are used to effect the pH adjustment. This demonstrates that a mixture of acids can be used to achieve the desired balance needed for recycle of the recovered sodium hydrogen maleate.

EXAMPLE 18

The procedure of Example 1 was repeated with the following charge:

| Water | 143.3 g | (to give 60% solids reaction) |
|---|---|---|
| 50% Sodium Hydroxide | 320.0 g | 4.0 moles |
| Malic Acid | 134.0 g | 1.0 mole |
| Calcium Hydroxide | 118.4 g | 1.6 mole |
| Maleic Anhydride | 245.0 g | 2.5 moles |

The reaction was run at 80-85° C. for three hours. At the end of the reaction, 100 g water were added and then a solution of maleic acid (116.0 g, 1.0 mole) and 88% formic acid (26.2 g, 0.5 mole) were added. The resulting pH of the reaction mass was 4.75. After cooling to about 30° C. the mass was filtered to give a filter cake of sodium hydrogen maleate, 521.9 g, and a filtrate weighing 898.7 g. Both were sampled for analysis.

A solution of sodium carbonate (220.5 g, 2.08 mole) in 600 g water was prepared and heated to about 80° C. The filtrate was added to the sodium carbonate solution while maintaining the temperature at near 80° C. The filtrate was added to the sodium carbonate solution while maintaining the temperature at near 80° C. At the end of the addition, 6 ml 50% NaOH was added to the mixture to adjust the pH from 10.17 to 10.40. The slurry was heated at 80-85° C. for one hour and then filtered hot. The calcium carbonate filter cake was washed with about 50 ml water. The filtrate, 1599.5 g, containing the desired tetrasodium oxydisuccinate, was sampled for analysis. Analytical results of the reaction mixture and filter cake appear in Table XVIII below (normalized weight %).

TABLE XVIII

| SAMPLE: COMPONENT | END OF REACTION | AFTER MALEATE REMOVAL | NaHMal FILTER CAKE | AFTER CARBONATE REMOVAL |
|---|---|---|---|---|
| Disodium Malate | 3.51 | 7.60 | 0.88 | 7.63 |
| Disodium Maleate | 33.36 | 1.82 | 89.52 | 2.26 |
| Disodium Fumarate | 5.73 | 8.49 | 0.96 | 8.63 |
| Tetrasodium Oxydisuccinate | 57.40 | 82.09 | 8.65 | 81.49 |
| Malate Conversion (Mole %) | 89.60 | 85.05 | — | 84.90 |

This example shows that even higher levels of maleate can be removed from the reaction mixture by this technique and that acceptable product solutions can be obtained without further purification.

EXAMPLE 19

This example shows that the technique of sodium hydrogen maleate removal is effective even at lower malate/meleate ratios, in this case a ratio of 1/1.5 is employed. The procedure of Example 1 was repeated with the following charge:

TABLE XIX

| Water | 104.2 g | (to give 60% solids reaction) |
| 50% Sodium Hydroxide | 224.0 g | 2.8 moles |
| Malic Acid | 134.0 g | 1.0 mole |
| Calcium Hydroxide | 88.8 g | 1.2 mole |
| Maleic Anhydride | 147.0 g | 1.5 mole |

The reaction was run at 80-85° C. for five hours. At the end of the reaction, 100 g were added and then a solution of maleic acid (58.0 g, 0.5 mole) was added resulting in a solution having a pH of 5.31. An additional 10.2 g of 88% formic acid (0.2 mole) was added to further reduce the pH. The resulting pH of the reaction mass was 5.03. After cooling to about 25° C. the mass was filtered to give a filter cake (washed with ca. 100 ml of water) sodium hydrogen maleate, 223.0 g (damp), and a filtrate weighing 678.1 g. Both were sampled for analysis.

A solution of sodium carbonate (154.3 g, 1.456 mole) in 400 g water was prepared and heated to ~80° C. The filtrate was added to the sodium carbonate solution while maintaining the temperature at near 80° C. The slurry was heated at 80-85° C. for one hour and then filtered hot. The calcium carbonate filter cake was washed with about 50 ml water. The filtrate, 1113.4 g, containing the desired tetrasodium oxydisuccinate, was sampled for analysis. Analytical results of the reaction mixture and filter cake (normalized weight %) are reported in Table XIX below.

TABLE XIX

| SAMPLE: COMPONENT | END OF REACTION | AFTER MALEATE REMOVAL | NaHMal FILTER CAKE | AFTER CARBONATE REMOVAL |
|---|---|---|---|---|
| Disodium Malate | 8.33 | 10.99 | 1.15 | 10.56 |
| Disodium Maleate | 18.99 | 1.83 | 88.23 | 1.54 |
| Disodium Fumarate | 5.68 | 7.07 | 0.92 | 7.03 |
| Tetrasodium Oxydisuccinate | 67.01 | 80.11 | 9.70 | 80.87 |
| Malate Conversion (Mole %) | 80.90 | 79.33 | — | 80.13 |

This example shows that the technique of sodium hydrogen maleate precipitation is effective at lower malate/maleate ratios (in this case 1/1.5). However, it is also seen that at the end of the reaction, considerable disodium malate remains in the reaction mixture, unreacted even after the longer reaction time at 80° C. (5 hours vs. 3 hours). This is due to the smaller excess amount of maleate present which does not drive the equilibrium reaction as far towards the desired ODS.

EXAMPLE 20

This example shows how conditions can be manipulated to increase the overall conversion of malate to ODS by combining the precipitation of sodium hydrogen maleate with the maturation procedure.

The following materials were charged to the 1 liter Ace reactor as described in Example 15:

| Water | 148.5 g | (to give 60% solids reaction) |
| 50% Sodium Hydroxide | 256.0 g | 3.2 moles |
| Malic Acid | 134.0 g | 1.0 mole |
| Calcium Hydroxide | 118.4 g | 1.6 mole |
| Maleic Anhydride | 196.0 g | 2.0 mole |

The addition of maleic anhydride was made at such a rate that the reaction temperature remained between 80 and 85° C. At the end of the addition, the reaction mass was sampled for analysis, heating was stopped and the reaction mass cooled to 40° C. and maintained at that temperature for 46 hours. At the end of this time, the reaction mass was sampled for analysis, diluted with 100 g water and reheated to 60° C. Then a solution of 116 g (1 mole) of maleic acid in 200 g water was added and the mass cooled providing a solution having a pH of 5.1. The product was filtered and the filter cake washed with a small amount of water. The filtrate (828.2 g) and the filter cake (393.0 g) were samples for analysis.

The filtrate was then added slowly to a hot (80° C.) solution of sodium carbonate (220.5 g, 2.08 mole) in 600 ml water. The slurry was heated at 82-88° C. for one hour and then filtered while hot. The filtrate, containing the desired tetrasodium oxydisuccinate, was sampled for analyses. Analytical Results of the reaction mixture and filter cake (normalized weight %) appear in Table XX below.

TABLE XX

| SAMPLE: | END OF ADDITION | END OF REACTION | AFTER MALEATE REMOVAL | NaHMal FILTER CAKE | AFTER CARBONATE REMOVAL |
|---|---|---|---|---|---|
| Disodium Malate | 20.49 | 1.36 | 2.43 | 0.42 | 2.70 |
| Disodium Maleate | 51.34 | 29.39 | 9.00 | 85.53 | 9.11 |
| Disodium Fumarate | 0.94 | 3.51 | 4.39 | 0.72 | 4.53 |
| Tetrasodium Oxydisuccinate | 27.24 | 65.77 | 84.18 | 13.33 | 83.66 |
| Malate Conversion (Mole %) | 41.18 | 96.22 | 94.80 | — | 94.23 |

This example shows that a combination of sodium hydrogen maleate removal and lower temperature reaction after initial high temperature reaction are effective in achieving high malate conversion. Also in this case, less sodium hydrogen maleate removal is noted since the upper end of the preferred pH region was attained.

There has been described a novel process of general application for the production of ether carboxylates. While the process has been described with reference to specific compounds no intention is made by such reference to limit the scope of this invention unless expressly stated. Various modifications may be made in the materials and sequence of process steps as well as process combinations which are adapted to suit the various reactants and products without departing from this invention.

I claim:

1. A process for preparing ether carboxylates which comprises reacting in an alkaline reaction medium the salts of maleic acid and a carboxylic or polycarboxylic acid having a reactive hydroxyl group on a non-carbonyl carbon atom in the presence of calcium ion catalyst, reducing the pH of the reaction product to a range of from about 4 to about 6 whereby unreacted starting acids are precipitated, recovering said acids from the reaction product for reuse in said process.

2. A process of claim 1 wherein the acid salt having a reactive hydroxyl group is a polycarboxylic acid.

3. A process of claim 2 wherein the polycarboxylic acid is malic acid.

4. A process of claim 1 wherein the polycarboxylic acid is tartaric acid.

5. A process of claim 1 wherein the pH is reduced to within the range of from about 4.8 to about 5.5.

6. A process of claim 1 wherein the pH is reduced by combining the reaction product with an organic acid.

7. A process of claim 6 wherein the organic acid is selected from the group consisting of formic, acetic, propionic, citric, maleic, tartaric, fumaric, malic, malonic, succinic, adipic, butyric and long chain fatty acids.

8. A process of claim 1 wherein the pH is reduced by combining the reaction product with an inorganic acid.

9. A process of claim 8 wherein the inorganic acid is selected from the group consisting of sulfuric, hydrochloric, carbonic, nitric, phosphoric, phosphorous, sulfonic and sulfurous acids.

10. A process of claim 1 wherein the pH is reduced by combining the reaction product with a mixture of organic and inorganic acid.

11. A process of claim 10 wherein the acids are sulfuric and maleic acids.

12. A process of claim 1 wherein the pH is reduced by adding the reaction product to an acid heel.

13. A process of claim 12 werein acid heel contains a mixture of two acids.

14. A process of claim 13 wherein the acids in the heel are formic and maleic.

15. A process of claim 1 further including the step of reducing the amount of calcium in the reaction product after removal of the unreacted starting acids by means of increasing the pH of the remaining solution to within a range of from about 7 to about 12 and combining the reaction product with a basic carbonate whereby calcium carbonate precipitates and is removed from the reaction product.

16. A process of claim 15 wherein the basic carbonate is sodium carbonate.

17. A process for preparing a mixture of the alkali metal salt of 1-hydroxy-3-oxa-1,2,4,5-pentane tetracarboxylic acid and 3,6-dioxa-1,2,4,5,7,8-octane hexacarboxylic acid which comprises the steps of:
    (a) forming an aqueous reaction mixture comprising from about 20% to 60% by weight of both calcium and monovalent cation salts of maleic acid and tartaric acid, said mixture corresponding to the over-neutralized mixture which is formed by combining:
        (i) maleic and tartaric acids in a maleic to tartaric molar ratio of from about 0.5:1 to about 8:1;
        (ii) a source of calcium cations in an amount such that the molar ratio of calcium to tartaric acid ranges from about 0.1:1 to 2.0:1 with the ratio of moles of calcium to total moles of maleic and tartaric acid being less than 1; and
        (iii) a neutralizing agent comprising a hydroxide of a monovalent cation in an amount such that the ratio of moles of monovalent cation to moles of maleic acid plus moles of tartaric acid minus moles of calcium ranges from about 2.1:1 to 3.8:1.
    (b) maintaining said aqueous reaction mixture at a temperature of from about 20° C. to 120° C. for a time period sufficient to form a reaction product mixture of said 1-hydroxy-3-oxa-1,2,4,5-pentane tetracarboxylic acid salts and 3,6-dioxa-1,2,4,5,7,8-octane hexacarboxylic acid salts;
    (c) lowering the pH of reaction mixture of step (b) to the range of from about 4.5 to about 5.5 and cooling the mixture to precipitate calcium tartrate and monosodium maleate;

(d) removing the precipitate from the reaction mixture formed in step (c) and recycling it to step (a) to prepare additional amounts of reaction product.

(e) treating the reaction mixture from step (d) with a carbonate or bicarbonate whereby calcium carbonate precipitates.

(f) removing the calcium carbonate from the reaction mixture of step (e) and recycling it to step (a) to prepare additional amounts of reaction product and (g) recovering and purifying the reaction mixture from step (f).

18. A process of claim 17 wherein the carbonate is an alkali metal carbonate.

19. A process of claim 18 wherein the alkali metal is sodium.

20. A process of claim 17 wherein the bicarbonate is sodium bicarbonate.

21. A process of claim 17 wherein the pH of the filtrate of step (d) is in the range of from 9 to 11 before combining with the carbonate.

22. A process of claim 17 wherein the mole ratio of carbonate to calcium in step (d) is 1.3:1.0.

23. A process of claim 17 wherein the neutralizing agent is sodium hydroxide.

24. A process of claim 17 wherein the pH of the reaction medium in step (c) is lowered by addition of an organic acid.

25. A process of claim 24 wherein the organic acid is selected from the group consisting of formic, acetic, propionic citric, maleic, tartaric, fumaric, malic, malonic, succinic, adipic, butyric and long chain fatty acids and a mixture thereof.

26. A process of claim 17 wherein the pH of the reaction medium is lowered by addition of an inorganic acid.

27. A process of claim 26 wherein the inorganic acid is selected from the group consisting of sulfuric, hydrochloric, carbonic, nitric, phosphoric, phosphorous, sulfonic and sulfurous acids or a mixture thereof.

28. A process of claim 17 wherein the temperature of the reaction medium in step (c) is lowered partially and then lowered to a temperature in the range of from at least above the freezing point of the mixture to about 40° C. slowly.

29. A process of claim 28 further including the step of allowing the cooled reaction medium to rest for a period of about 30 minutes prior to separation of the precipitate.

30. A process of claim 28 further including the step of removing water from the reaction medium during cooling.

31. A process of claim 28 wherein the pH is lowered in step (c) by addition of a mixture of acids.

32. A process for preparing a mixture of the alkali metal salt of 1-hydroxy-3-oxa-1,2,4,5-pentane tetracarboxylic acid and 3,6-dioxa-1,2,4,5,7,8-octane hexacarboxylic acid which comprises the steps of:

(a) forming an aqueous reaction mixture comprising from about 20% to 60% by weight of both calcium and monovalent cation salts of maleic acid and tartaric acid, said mixture corresponding to the over-neutralized mixture which is formed by combining:

(i) maleic and tartaric acids in a maleic to tartaric molar ratio of from about 0.5:1 to about 8:1;

(ii) a source of calcium cations in an amount such that the molar ratio of calcium to tartaric acid ranges from about 0.1:1 to 2.0:1 with the ratio of moles of calcium to total moles of maleic and tartaric acid being less than 1; and (iii) a neutralizing agent comprising a hydroxide of a monovalent cation in an amount such that the ratio of moles of monovalent cation to moles of maleic acid plus moles of tartaric acid minus moles of calcium ranges from about 2.1:1 to 3.8:1.

(b) maintaining said aqueous reaction mixture at a temperature of from about 20° C. to 120° C. for a time period sufficient to form a reaction product mixture of said 1-hydroxy-3-oxa-1,2,4,5-pentane tetracarboxylic acid salts and 3,6-dioxa-1,2,4,5,7,8-octane hexacarboxylic acid salts;

(c) adjusting the pH of reaction mixture of step (b) to the range of from about 9.0 to about 10.5 and cooling the mixture to precipitate calcium tartrate;

(d) removing the precipitate formed in step (c) from the reaction mixture and recycling it to step (a) to prepare additional amounts of reaction product;

(e) treating the reaction mixture from step (d) with a carbonate or bicarbonate whereby calcium carbonate precipitates. (f) removing the calcium carbonate from the reaction mixture of step (e) and recycling it to step (a) to prepare additional amounts of reaction product; and (g) lowering the pH of the solution remaining after removal of calcium carbonate in step (f) to a range of from about 4.5 to about 5.5 whereby monosodium maleate precipitates;

(h) removing the monosodium maleate from the filtrate and recycling it to step (a) to prepare additional amounts of reaction product; and (i) recovering and purifying the reaction mixture from step (h).

33. A process of claim 32 wherein the pH is lowered in step (c) by combination of the reaction mixture with formic acid.

34. A process of claim 32 wherein the pH is lowered in step (g) by combining the filtrate with maleic acid.

35. A process for preparing ether carboxylates which comprises reacting in an alkaline reaction medium the salts of maleic acid and malic acid in the presence of calcium ion catalyst, reducing the pH of the reaction product to a range of from about 4 to about 6 whereby monosodium maleate is precipitated, recovering said acids from the reaction product for reuse in said process and recovering 2,2'-oxydisuccinate from solution.

36. A process of claim 35 wherein the calcium ion is provided by calcium hydroxide, and the alkalinity is provided by sodium hydroxide.

37. A process of claim 36 wherein the mole ratio of malic acid/maleic acid/calcium hydroxide/sodium hydroxide is in the range of from about 1/2/1.6/3 to about 1/2.5/2/3.2 respectively.

38. A process of claim 35 wherein the pH is reduced to a range of from about 4.8 to about 5.2.

39. A process of claim 35 wherein the reaction temperature is in the range of from about 60° C. to about 110° C.

40. A process of claim 39 wherein the reaction temperature is in the range of from about 70° C. to about 80° C.

41. A process of claim 37 wherein the reaction temperature is in the range of from about 70° C. to about 90° C. and the reaction time is from about 1.5 hours to about 6 hours.

42. A process of claim 35 wherein the solution of 2,2'-oxydisuccinate is treated with a basic carbonate to raise the pH of the solution to about 7 to about 12 whereby calcium carbonate precipitates and is recycled for use in preparing additional 2,2'-oxydisuccinate.

43. A process of claim 42 wherein the pH is raised to the range of from about 10 to about 10.5.

44. A process of claim 43 wherein the solution is held at said pH for a period of from about 1 to about 2 hours prior to removing the calcium carbonate.

45. A process of claim 42 wherein the precipitate is removed while the solution is at a temperature in the range of from about 75° C. to about 85° C.

46. A process for preparing ether carboxylates which comprises reacting in an alkaline reaction medium the salts of maleic acid and a carboxylic or polycarboxylic acid having a reactive hydroxyl group on a non-carbonyl carbon atom in the presence of calcium ion, reducing the pH of the reaction product to a range of from about 4 to about 6 whereby unreacted starting acids are precipitated, recovering said acids from the reaction product for reuse in said process, then increasing the pH of the remainder of the reaction mixture by addition of a carbonate or bicarbonate whereby calcium carbonate precipitates and is removed from the reaction mixture, reacting said calcium carbonate with maleic acid to form a calcium salt of said acid for use in said process.

47. A process for preparing a mixture of the alkali metal salt of 1-hydroxy-3-oxa-1,2,4,5-pentane tetracarboxylic acid and 3,6-dioxa-1,2,4,5,7,8-octane hexacarboxylic acid which comprises the steps of:
(a) forming an aqueous reaction mixture comprising from about 20% to 60% by weight of both calcium and monovalent cation salts of maleic acid and tartaric acid, said mixture corresponding to the over-neutralized mixture which is formed by combining:
(i) maleic and tartaric acids in a maleic to tartaric molar ratio of from about 0.5:1 to about 8:1;
(ii) a source of calcium cations in an amount such that the molar ratio of calcium to tartaric acid ranges from about 0.1:1 to 2.0:1 with the ratio of moles of calcium to total moles of maleic and tartaric acid being less than 1; and
(iii) a neutralizing agent comprising a hydroxide of a monovalent cation in an amount such that the ratio of moles of monovalent cation to moles of maleic acid plus moles of tartaric acid minus moles of calcium ranges from about 2.1:1 to 3.8:1.
(b) maintaining said aqueous reaction mixture at a temperature of from about 20° C. to 120° C. for a time period sufficient to form a reaction product mixture of said 1-hydroxy-3-oxa-1,2,4,5-pentane tetracarboxylic acid salts and 3,6-dioxa-1,2,4,5,7,8-octane hexacarboxylic acid salts;
(c) lowering the pH of reaction mixture of step(b) to the range of from about 4.5 to about 5.5 and cooling the mixture to precipitate calcium tartrate and monosodium maleate;
(d) removing the precipitate from the reaction mixture formed in step (c) and recycling it to step (a) to prepare additional amounts of reaction product;
(e) treating the reaction mixture from step (d) with a carbonate or bicarbonate whereby calcium carbonate precipitates;
(f) removing the calcium carbonate from the reaction mixture of step (e) and reacting said carbonate with maleic acid to form a calcium salt of maleic acid;
(g) employing said calcium salt of maleic acid to prepare additional ether carboxylates in step (a) above; and
(h) recovering and purifying the reaction mixture from step (f).

48. A process for preparing a mixture of the alkali metal salt of 1-hydroxy-3-oxa-1,2,4,5-pentane tetracarboxylic acid and 3,6-dioxa-1,2,4,5,7,8-octane hexacarboxylic acid which comprises the steps of:
(a) forming an aqueous reaction mixture comprising from about 20% to 60 % by weight of both calcium and monovalent cation salts of maleic acid and tartaric acid, said mixture corresponding to the over-neutralized mixture which is formed by combining:
(i) maleic and tartaric acids in a maleic to tartaric molar ratio of from about 0.5:1 to about 8:1;
(ii) a source of calcium cations in an amount such that the molar ratio of calcium to tartaric acid ranges from about 0.1:1 to 2.0:1 with the ratio of moles of calcium to total moles of maleic and tartaric acid being less than 1; and
(iii) a neutralizing agent comprising a hydroxide of a monovalent cation in an amount such that the ratio of moles of monovalent cation to moles of maleic acid plus moles of tartaric acid minus moles of calcium ranges from about 2.1:1 to 3.8:1.
(b) maintaining said aqueous reaction mixture at a temperature of from about 20° C. to 120° C. for a time period sufficient to form a reaction product mixture of said 1-hydroxy-3-oxa-1,2,4,5-pentane tetracarboxylic acid salts and 3,6-dioxa-1,2,4,5,7,8-octane hexacarboxylic acid salts;
(c) lowering the pH of reaction mixture of step(b) to the range of from about 4.5 to about 5.5 and cooling the mixture to precipitate calcium tartrate and monosodium maleate;
(d) removing the precipitate from the reaction mixture formed in step (c), then reacting said precipitate with calcium carbonate and sufficient maleic acid to convert the monosodium maleate to calcium maleate and employing said maleate in step (a);
(e) treating the reaction mixture from step (d) with a carbonate or bicarbonate whereby calcium carbonate precipitates;
(f) removing the calcium carbonate from the reaction mixture of step (e) and reacting said carbonate with maleic acid to form a calcium salt of maleic acid;
(g) employing said calcium salt of maleic acid in step (a) above, and
(h) recovering and purifying the reaction mixture from step (f).

49. A process of claim 48 wherein the maleic acid is formed in situ from maleic anhydride and water.

* * * * *